(12) United States Patent
Birkenbach et al.

(10) Patent No.: US 7,203,277 B2
(45) Date of Patent: Apr. 10, 2007

(54) VISUALIZATION DEVICE AND METHOD FOR COMBINED PATIENT AND OBJECT IMAGE DATA

(75) Inventors: Rainer Birkenbach, Aufkirchen (DE); Robert Schmidt, München (DE); Richard Wohlgemuth, München (DE); Holger-Claus Rossner, Feldkirchen (DE); Nils Frielinghaus, Heimstetten (DE); Claus Schaffrath, München (DE); Swen Wörlein, München (DE)

(73) Assignee: BrainLAB AG, Feldkirchen (DE)

( * ) Notice: Subject to any disclaimer, the term of this patent is extended or adjusted under 35 U.S.C. 154(b) by 99 days.

(21) Appl. No.: 10/830,963

(22) Filed: Apr. 23, 2004

(65) Prior Publication Data

US 2004/0263535 A1 Dec. 30, 2004

Related U.S. Application Data

(60) Provisional application No. 60/489,750, filed on Jul. 24, 2003.

(30) Foreign Application Priority Data

Apr. 25, 2003 (EP) .................................. 03008840

(51) Int. Cl.
*H05G 1/00* (2006.01)
(52) U.S. Cl. ..................................... 378/98.5; 378/205
(58) Field of Classification Search ................ 378/205, 378/98.5, 206, 195, 198, 208, 197, 98.12, 378/98, 98.2; 600/410, 411, 414, 418, 425, 600/426, 427
See application file for complete search history.

(56) References Cited

U.S. PATENT DOCUMENTS 5,978,143 A 11/1999 Spruck

| | | | |
|---|---|---|---|
| 6,038,467 A * | 3/2000 | De Bliek et al. ............ 600/424 |
| 6,644,852 B2 * | 11/2003 | Crain et al. ................. 378/197 |
| 2002/0082498 A1 | 6/2002 | Wendt et al. | |
| 2005/0020909 A1 * | 1/2005 | Moctezuma de la Barrera et al. ........................... 600/424 |

FOREIGN PATENT DOCUMENTS

| EP | 0 877 274 | 11/1998 |
| EP | 1 321 105 | 6/2003 |
| WO | 00/36845 | 6/2000 |
| WO | 03/002011 | 1/2003 |

OTHER PUBLICATIONS

Search Report for European counterpart application No. EP 04 01 7859 dated Jan. 12, 2005.

* cited by examiner

*Primary Examiner*—Edward J. Glick
*Assistant Examiner*—Hoon Song
(74) *Attorney, Agent, or Firm*—Renner, Otto, Boisselle and Sklar, LLP

(57) ABSTRACT

A device for visually combining patient image data from transillumination and/or tomographic imaging methods with object image data comprising video images includes an image display device and at least one video camera associated with the image display device as a portable unit. A computer-assisted navigation system can detect the spatial positions of the image display device and/or the video camera as well as the spatial positions of a part of the patient's body via tracking means. An input device can be provided on the image display device, which enables inputs for image-assisted treatment or treatment planning.

20 Claims, 3 Drawing Sheets

VISUALIZATION DEVICE AND METHOD FOR COMBINED PATIENT AND OBJECT IMAGE DATA

RELATED APPLICATION DATA

This application claims priority of U.S. Provisional Application No. 60/489,750, filed on Jul. 24, 2003, which is incorporated herein by reference in its entirety.

FIELD OF THE INVENTION

The invention relates to visualizing combined patient and object image data in systems in which patient image data or object image data are projected onto video images.

BACKGROUND OF THE INVENTION

Devices for visualizing patient and object image data typically include an image display means, at least one video camera and a computer-assisted navigation system, which can detect the spatial positions of the display device and/or the video camera as well as the spatial position of a part of the patient's body via tracking means attached to it. The devices serve to visually assist a physician when diagnosing and/or treating a patient. The intention is to provide the option of combining images from the interior of the patient with conventional video images, to order to facilitate treatment and diagnosis.

A generic, video-based surgical target system is known from U.S. Pat. No. 5,765,561, in which the use of a tracked camera is proposed, where the images from which are superimposed together with associated images from transillumination and/or tomographic imaging methods on the statically arranged screen of a navigation system. U.S. Pat. No. 5,715,836 also describes superimposing images from different sources in an operation or treatment environment. The images can come from computer tomography, nuclear spin tomography, ultrasound or x-ray image apparatus. Here too the images are outputted on a stationary screen.

Positional verification for positional markings in a video camera image, wherein video cameras and infrared cameras are combined and their images superimposed, is known from DE 19 848 765 A1. Here too the images are outputted on a stationary screen.

A disadvantage of the devices described above is that a physician who wishes to view the images always has to look away from the patient to the screen of the navigation system. He can thus no longer pay exact attention to what position the camera is then in, i.e., from what exterior position exactly he is receiving the superimposed images. The system is, therefore, awkward and does not enable a direct view into the part of the patient's body. Furthermore, all the inputs that the physician proposes to make into the system have to be made at the input station of the navigation system or treatment planning system. Thus, the physician again has to turn away from the patient and cannot directly verify the effect of the inputs.

SUMMARY OF THE INVENTION

In accordance with one aspect of the invention, the invention is directed to a device and/or method for visually combining patient image data from transillumination and/or tomographic imaging methods and/or object image data comprising video images, which overcome the disadvantages of the prior art. The device and/or method can enable desired image information to be received directly and in the direct view of the patient and thus to also exercise an influence on assisting the treatment.

In accordance with one aspect of the invention, the invention is directed to a device in which an image display device and a video camera are associated with each other and are formed as a portable unit, and an input device is provided on the image display device, which enables inputs for image-assisted treatment or treatment planning.

This enables the physician carrying out the treatment to hold the image display device himself, with the associated camera, in front of the part of the patient's body and to read off the desired anatomical information while looking directly at the patient. Just by associating the video camera and image display device and forming them as a portable unit, the device in accordance with the invention takes another step towards creating a "glass patient", the image display device merely having to be held in front of the part of the patient's body in question. Since the association of the camera to the image display device is tracked via the tracking means, the position of the elements viewed is always known, and the navigation system has information on how and from which direction the part of the patient's body is being viewed. For example, when performing minimally invasive surgery, in which no area operated on is exposed, the device in accordance with the invention thus offers the physician carrying out the treatment the option, during the operation, of exactly apprizing himself once again of the position of the patient's anatomical parts and/or of other objects in relation to the patient's anatomy. Tracked and/or navigated instruments can also be displayed on the image display device. The physician no longer has to look away from the patient in order to look into the interior of the patient's body.

In addition, the physician is put into a position to make changes and modifications which assist his work, via the input device, while still directly viewing the patient and with the aid of information from the image display. He can then verify the effect of his modifications directly and while viewing the patient without having to firstly turn toward an input station, which makes verifying or correcting particular measures much simpler and more direct.

In a preferred embodiment of the invention, the input device includes electro-mechanical switches. These switches can be of any known type, such as push switches, directional push switches, as well as, joystick-like switches, integrated or combined with push switches, are conceivable. A number of input devices of the aforementioned types can be provided. It is equally possible to form the input device additionally or solely as a touch screen. Any possible input device can be realized, even advanced ones, such as speech inputs and the like.

In accordance with one embodiment of the device, the device can be associated with a computer-assisted treatment planning and assisting system, which processes inputs from the input device. The portable unit, including the image display device and the video camera, thus becomes a part of the treatment planning system and of assisting the treatment and saves on corresponding separate input to system devices provided separately for said purpose.

The device in accordance with the invention can include cable-assisted or cable-free data transmission between the image display device and the computer-assisted treatment planning and assisting system, by means of which object information is transmitted, preferably in response to an input. Such object information can include all types of image information and can be transmitted in both directions, for exchanging and comparing information.

The invention further relates to a method for visually combining patient image data from transillumination and/or tomographic imaging methods and/or object image data comprising video images on an image display means which is associated with at least one video camera. A computer-assisted navigation system detects the spatial position of the image display device and/or the video camera and the spatial position of a part of the patient's body via tracking means attached to it, the image display device and the video camera being formed as a portable unit, and inputs for image-assisted treatment or treatment planning being inputted by means of an input device on the image display device.

In one embodiment of the method in accordance with the invention, a computer-assisted treatment planning and assisting system processes the inputs from the input device. Treatment-assisting object and/or image information can thus be transmitted via cable-assisted or cable-free data transmission between the image display device and the computer-assisted treatment planning and assisting system. The object and/or image information can include one or more of the following types of information: information on patient-specific parts of the patient's body obtained from two-dimensional or three-dimensional image data; information on non-patient-specific, model-based object data, such as generic or adapted generic parts of the body such as bones or soft tissues; information on implants; measurement information; information on medicines, and specifically their distribution, also simulated distribution; information on radiosurgical and radiotherapeutic plans; information on plans for image-assisted surgery; information on registering markers; information on instruments; and x-ray images artificially generated from image data information (DDRs=digitally reconstructed radiographs) and/or information from actual x-ray images.

A method in accordance with the invention can be designed such that treatment-assisting image or object data or treatment plans are changed or adapted by inputs at the input device. Furthermore, image representation at the image display means can be changed or adapted by such inputs.

In accordance with another embodiment, changes to the patient body predicted by planning are displayed on the image display device by inputs at the input device. This enables planning to be directly controlled while directly viewing the part of the patient's body.

Another embodiment of the method in accordance with the invention is characterized by images on the image display device being stored, combined, spliced into image sequences or films, forwarded, played back, subtracted from each other or annotated, by inputs at the input device, wherein these actions can be performed individually or in any combination.

In one embodiment, other apparatuses in the treatment environment are controlled by inputs at the input device.

It is possible to integrate the image display means by directly attaching it to an imaging apparatus for the computer-assisted treatment planning and assisting system.

General embodiment variants for the device in accordance with the invention are explained in the following. In one embodiment, the video camera can be arranged on the rear side of the image display device. This creates a compact apparatus, where the camera can be completely removed from the user's field of view. It should be noted that the camera can be attached to any point on the rear side of the image display device or integrated in it, e.g., even in the peripheral area of the image display device. The video camera can have a spatial association with the image display device, which is predetermined and/or known to the system, and the tracking means is arranged on the image display device. The fact that the spatial association between the video camera and the image display device is predetermined and/or known to the system opens up the possibility of tracking only one of these apparatuses by means of the tracking means, since it is exactly known where the other apparatus is then situated. The designer is then free to arrange the tracking means either on the image display device itself or on the video camera, depending on how the tracking means can best be detected by the navigation system. In the case of optically based navigation systems, the tracking means can be a reflective or actively emitting marker arrangement, while it is also possible within the context of the present invention to navigate via a magnetic tracking system in which coils are tracked in a generated magnetic field. As far as navigation and/or tracking systems which operate using reflective marker arrangements are concerned, those which operate using invisible light (e.g. infrared) and a corresponding light source may be used, but also those which use video technology the operates using visible light (ambient light). The latter systems use optical markers which reflect visible light, wherein, however, marker identification is analyzed only in the video image.

The image display device can be designed to be light and easy to handle, for example, by designing it as a portable flat-screen, such as an LCD flat-screen. As noted above, this screen can of course exhibit the touch screen function. The device in accordance with the invention can be supplied with power either by a power supply of its own (a battery or power pack) or via cables. If wireless, such as radio, transmission is used for the data, then a power supply of its own is particularly suitable for the device, in order to achieve the greatest freedom of handling.

The video camera can exhibit a small aperture and a low depth of field, so that only a small area of the captured image is in the focal plane. Using such a camera, it is possible ascertain the distance between the image and the focal plane. If the spatial position of the camera is known from the navigation system, and the distance from the image plane is likewise known, then the computer system connected to the navigation system can calculate the spatial position of the video image in real time. It is therefore possible to optimally associate the video image and the image data from previous transillumination and/or tomographic imaging, or equally to associate object data.

The individual image data and/or object data to be superimposed are advantageously adapted in size and position on the image display device, such that a correct and/or desired association of size results, for example, a 1:1 representation of the superimposed images. In the navigation system and/or in the treatment planning and assisting system, which can be provided as a part of the navigation system or separately and associated with it, a contour-matching unit can be provided by means of which the image data shown can be superimposed, in particular, via outer contour matching for the part of the patient's body.

An illuminating device for the part of the patient's body, specifically for example a ring light (LEDs, lamps, fluorescent tubes), is advantageously provided on the camera or in its vicinity on the image display device.

BRIEF DESCRIPTION OF THE DRAWINGS

These and further features of the present invention will be apparent with reference to the following description and drawings, wherein.

DETAILED DESCRIPTION OF THE INVENTION

Figure 1:
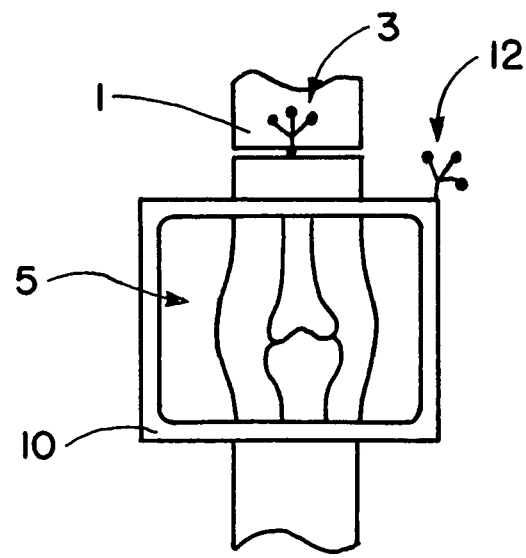
FIG. 1 is a schematic representation a device in accordance with the invention for viewing a patient's knee joint in aspect.

FIG. 1 schematically shows a device in accordance with the invention, with which, for example, it is possible to look into the interior of a patient's joint. In this exemplary embodiment, the patient's leg 1 is to be examined at the joint 5. For this purpose, the flat-screen 10 designed in accordance with the invention is held directly in front of the joint, an image then appears on the screen 10. The image contains both image information from the video camera image from the camera 14 (FIG. 2) and image information about the internal anatomical structure, which is relayed, for example, by radio transmission from a navigation apparatus. In addition, a tomograph (MR or CT image) of the patient and/or the patient's leg 1 has been produced in advance.

Figure 2:
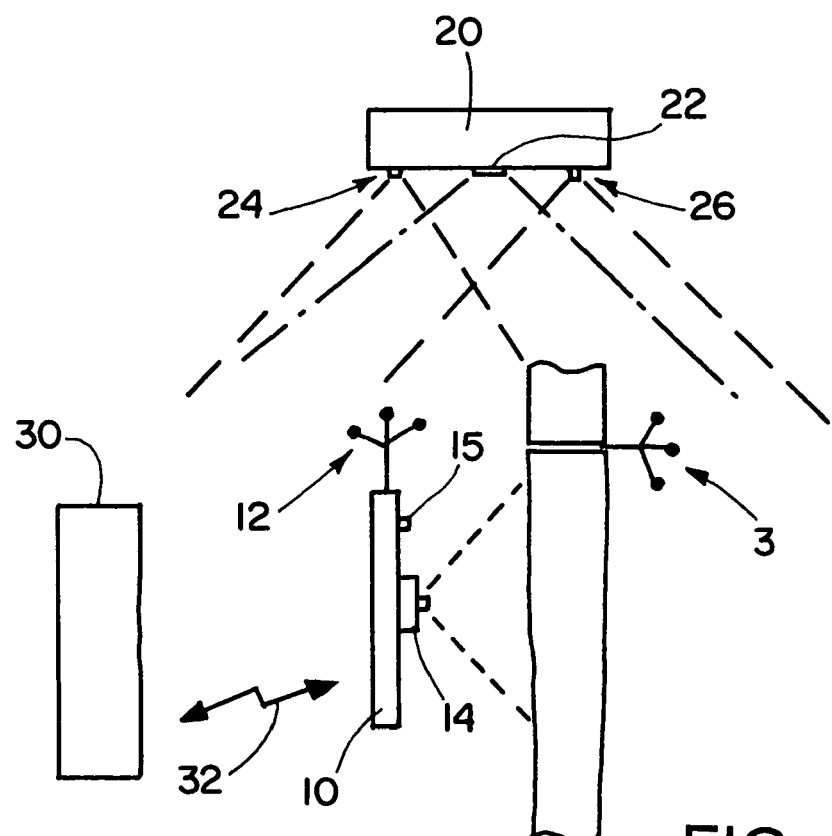
FIG. 2 is a lateral view of the device according to FIG. 1, with a schematically shown navigation system.

In one embodiment, shown in FIG. 2, the camera 14 is situated, fixedly attached, on the rear side of the screen 10.

This type of image representation is possible because the position of the camera 14 and/or the screen 10 in the space around the patient's leg 1 is ascertained using a tracking means 12. In the illustrated embodiment, the tracking means 12 is an optical tracking means, such as a marker arrangement, whose position is detected by means of the schematically shown navigation system 20. For this purpose, the navigation system 20 can include, for example, two spaced infrared cameras 24, 26 and an infrared light emitter 22. Such an exemplary navigation system is described more fully in co-owned U.S. Pat. No. 6,351,659, which is incorporated herein by reference in its entirety. The three-dimensional spatial position of the marker arrangement 12 and, therefore, also of the screen 10 and the fixedly installed camera 14 can be ascertained from the two images from the infrared cameras 24, 26. Furthermore, it is possible to ascertain the spatial position of the leg 1 using a corresponding marker arrangement 3 in space.

If the positions of the screen 10 and the camera 14 are then known, the position of the current image plane can be determined. Since the camera 14 has a small aperture and a low depth of field, the image only appears focussed in a particular focal plane. From this, the position of the image plane can be ascertained and an image from the CT or MR imaging method, which is also currently in this image plane, can be transmitted to the screen 10. In one embodiment, the mapping ratio of the video image is displayed on a scale of 1:1 with the tomograph. If the patient's joint is then viewed using the device in accordance with the invention, the contours of the patient's leg are for example seen at the upper and lower periphery of the image. Using this information, the image from the tomographic imaging method can then be adapted such that it lies directly over the video image in order to ensure a realistic impression. Someone viewing the screen 10 can then view both the video image, i.e., a real image, and the "internal" image from the tomographic imaging method on the screen, and in any desired depth and in any transparency set, respectively, for both images. These settings can be made via control devices and other inputs in accordance with the invention (which are discussed more fully below), such as the one indicated by the reference numeral 15.

This device gives the viewer the option of looking into the internal treatment area while looking directly at the patient, in real time, and to plan or adapt the treatment accordingly. He no longer has to turn away from the patient and look at a fixedly installed navigation screen, which is particularly advantageous when the patient's responses to particular medical measures are to be verified. Since the "internal" images from the transillumination and/or tomographic imaging methods can be formed such that they show virtual 3D views of the internal parts of the body, the image as a whole can be made very vivid.

Thus, although a transillumination and/or tomographic image is not taken in situ, a virtual "glass patient" is thus created.

Figure 3:
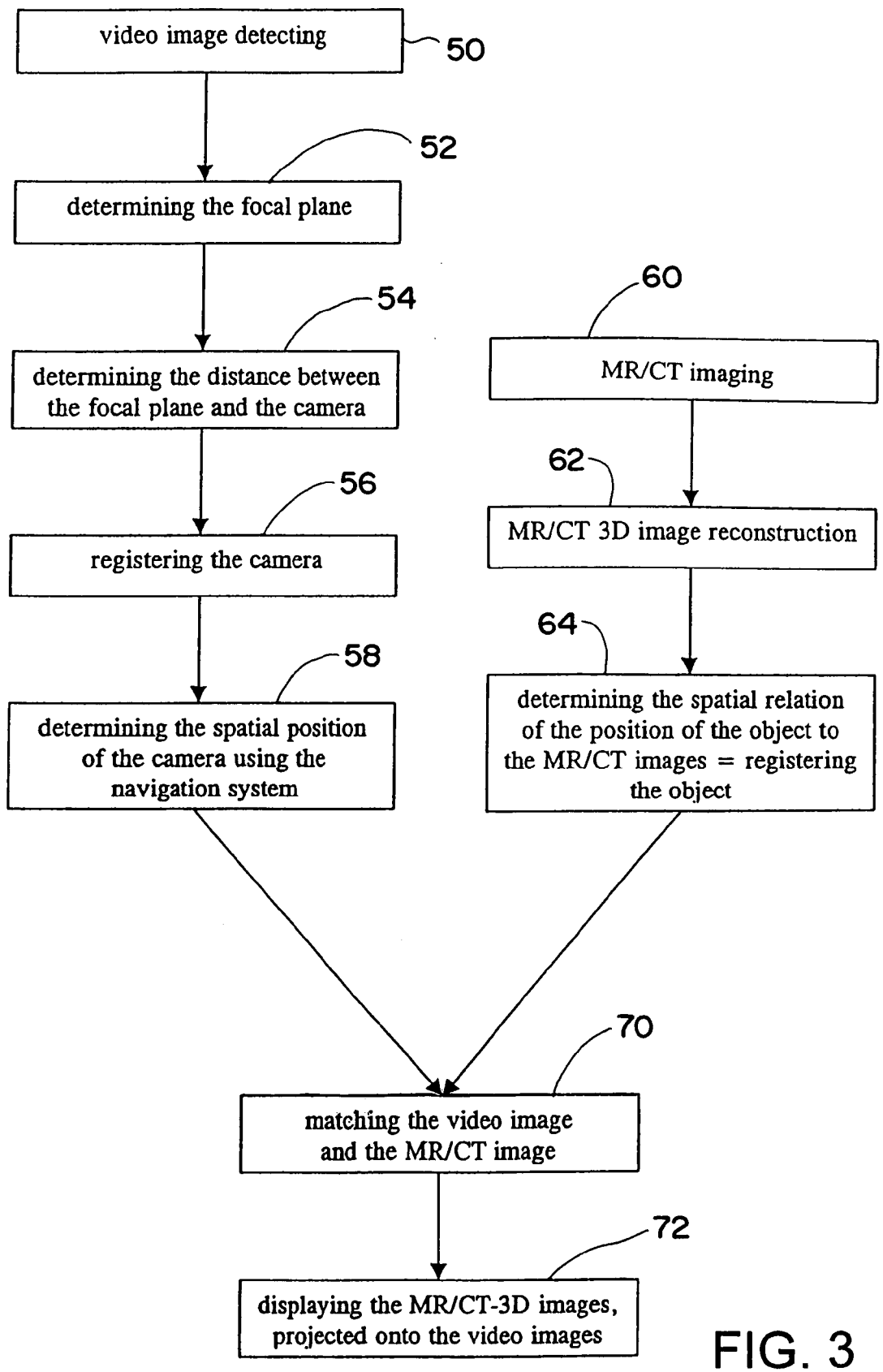
FIG. 3 is a flow diagram for operating the device in accordance with the invention.

FIG. 3 shows the progression of a method such as is performed using the device in accordance with the invention. It is to be appreciated that portions of the illustrated method can be performed by the computer of the navigation system is illuminated. The upper left-hand side of the flow diagram relates to the video imaging processes 50, while, on the right-hand side, the imaging for the interior of the body is explained, using the example of MR/CT imaging 60. During video imaging 50, the focal plane is first determined 52 as has already been explained above. Then the distance from the focal plane to the camera is determined 54, whereupon the camera is registered 56 in the navigation system by means of its tracking means. The determined spatial position of the camera relative to the navigation system is then known 58.

As far as the MR/CT imaging 60 is concerned, this will be performed first, in advance, whereupon a three-dimensional image reconstruction 62 is performed on the data obtained 60. The object, for example, a part of the patient's body, is then spatially registered 64, i.e., the relationship between the spatial position of the object and the MR/CT images is determined. This can be realized by spatially detecting a marker arrangement situated on the object.

When the steps cited above, of video imaging 50 and MR/CT image processing 60, 62, have been performed, video image/MR/CT image matching is then performed 70, i.e., the two images are harmonized under computer guidance, regarding image position and image size. Then, the MR/CT 3D images, which are projected 72 onto the video images on the image display device, can be superimposed and can assist the physician carrying out the treatment in his diagnosis and treatment.

In one embodiment, the transmitted object and/or image information can be x-ray images artificially generated from image data information (DDRs=digitally reconstructed radiographs), or information from actual x-ray images. In this case, for example, a diagnostic scan exists of the patient, such as a CT scan, and the portable flat-screen serves, so to speak, as an artificial x-ray film, i.e., the tracking and/or navigation system ascertains the position of the screen and knows the position of the patient and can then "beam rays" through the patient virtually, which, as with an x-ray apparatus, then result in an x-ray-like image. This gives the user the option of virtually holding an x-ray source in his hand and obtaining x-ray images from all viewing angles.

Figure 4:
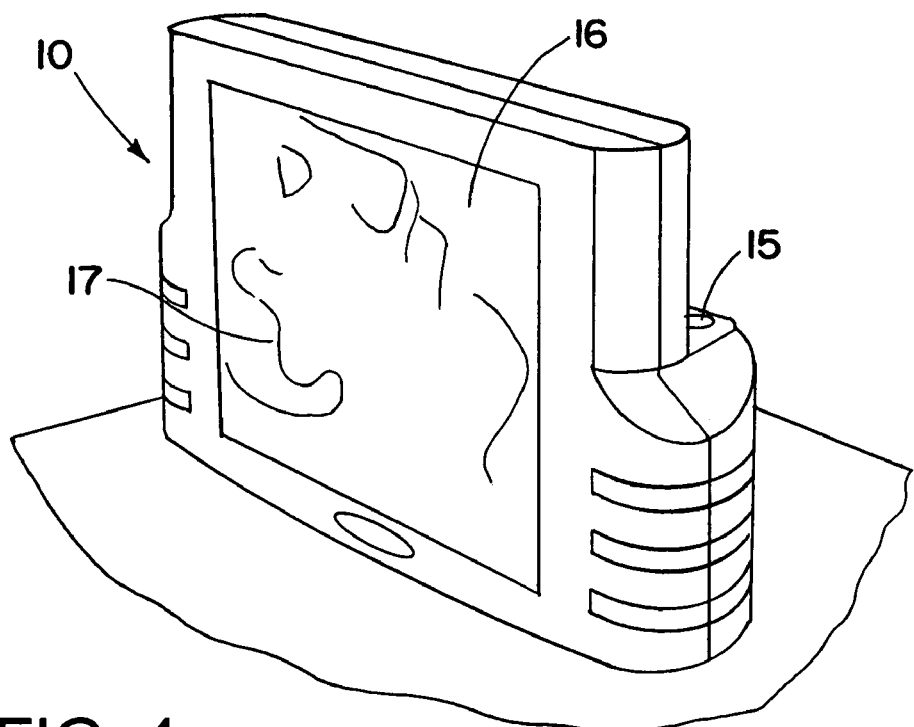
FIG. 4 is a perspective front view of a device in accordance with the invention.
Figure 5:
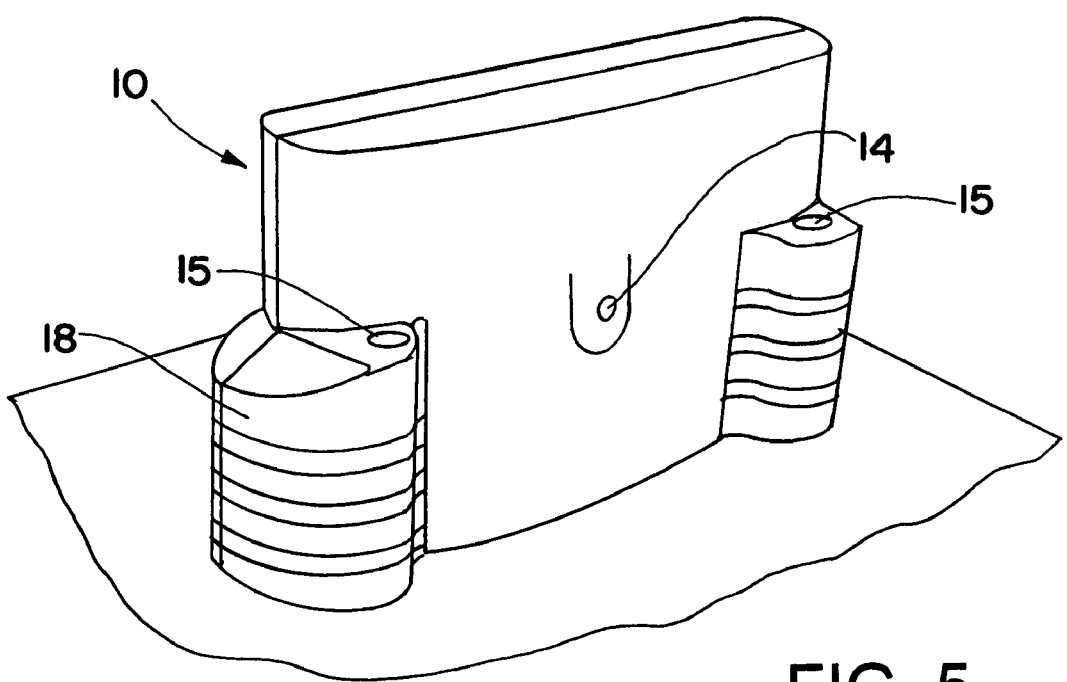
FIG. 5 is a perspective rear view of a device in accordance with the invention.

FIGS. 4 and 5 show, in perspective, an embodiment of the device in accordance with the invention, from the front and rear sides, respectively. In this case, the image display device 10 includes a screen 16, which can be formed as a touch screen. The video image of a patient, which has just been taken can be seen on the screen 16, and patient-specific objects, i.e., internal structures 17, are superimposed, for example, in the ear. The portable screen 10 additionally can include input buttons 15 arranged on the handle 18 at the top and/or on the handles on each side. The camera 14 is embedded centrally in the back of the apparatus.

Using these input buttons 15 and/or using the touch screen 16, inputs can then be made, which turn the device 10 into a multifunctional apparatus that can be used during treatment planning and/or treatment assisting. Referring again to FIG. 2, the device 10 can be connected to or otherwise associated with a conventional treatment assisting and/or planning system 30, for example, by radio, in order to exchange data. This data exchange can be accomplished using cable-assisted or cable free data transmission means 32, including, but not limited to, radio transmission, infrared transmission and the like. The associated computer-assisted treatment planning and assisting system can process inputs from input device. In this way, the following actions can specifically be performed individually or in combination.

Objects shown can be switched on or off, i.e., they are made visible or invisible. Parameters of objects shown, such as the color, transparency, etc., can be altered. The image can be zoomed in or out, and the brightness and/or contrast can be regulated on the screen. Objects can be marked and/or selected and moved, for example, for planning or modifying a treatment plan. Landmarks or measured sections can be set. It is possible to store screen shots of the image representation or to forward images for documentation. Film recordings consisting of a number of captured images can be played back, started or paused.

The working distance can be altered, (i.e., the "virtual depth of field") wherein it is established at what distance objects are visible. Planning options exist, for example, for planning trajectories and planes (bone section). It is possible to separately highlight particular areas of interest on the image representation, i.e., to direct a sort of spotlight onto particular areas.

Furthermore, the input means 15, 16 can be used to control other apparatuses, such as the navigation system, treatment robots, microscope, C-arc, ultrasound, ambient light, and the like. The image can be frozen, in particular, while the instruments continue to be navigated and projected. A differentiation of two or more images, preferably as before/after images, can be shown in response to an input. Similarly, an undo/redo function can be provided.

Panoramic images can be generated, for example, in order to map a complete, elongated part of the patient's body (e.g., a leg).

It is possible to input text, for example, to indicate points and to input comments regarding particular features shown. By controlling the inputs, the image display device can be used as an intelligent digital camera, also video camera, for the purposes of documentation, and extension sets are conceivable, which, for example, provide aids from data memories or the internet.

Another area of application is developed if, using the inputs, previews of body modifications can be superimposed, in order to show the physician, directly in situ and while viewing the patient, what the result of his treatment planning could look like. Within the context of the invention, the term "objects" is to be generally understood as a broad variety of image data information, on actual, bodily objects as well as on virtual image information material. This object information can be obtained from patient-specific, two-dimensional or three-dimensional data originating, for example, from imaging methods, such as CT, MR, functional MR, ultrasound, PET, SPECT, x-ray images, and the like. It is, however, equally possible to use model-based data, i.e., to work without data from the current patient. Bones, for example, come into consideration in this respect (tubular bones, cranium, bone fragments MKG, etc.), but also soft tissues (brain, ligaments, fluids, etc.). This data can then be adapted in size, or matching data or objects are selected from a set of available data or objects.

Other objects or object information relate to implants (hip, knee, teeth, intramedullary pins, screws, plates), such as implants in the spinal area (screws, artificial intervertebral discs, cages, internal/external fixtures), or also in the area of the brain (surface electrodes, deep brain stimulators, clips, coils, catheters, etc.). The implants can likewise be selected from predetermined sizes and virtually inserted on the image display device, to see which implant fits best where and what the result looks like.

It is furthermore possible to superimpose other objects or object information, such as, for example, measurement information (rulers, distances from the target area, etc.). Time simulations on the injection of administered medicines or their distribution over time can be requested by an input and shown visually, as with radiosurgical and/or radiotherapeutic plans and their predictable effects. Furthermore, the objects can of course include registering markers and instruments (endoscopes, saw, drill, awl, etc.).

Overall, it may be said that any information of interest, on objects or relating to objects, can be exchanged between the image display means and assisting systems, the data exchange also containing modifications to said objects and object information.

It is, for example, further possible to identify and obtain implants (skin, bone) in a first region and then to insert them in a second region. The obtained implants can possibly also be navigated in this way. In the field of spinal surgery, fixing elements, such as fixing rods, which are conventionally bent and adapted by hand, can be virtually adapted, i.e. planned, controlled by the image display device and using the information on the patient. In this way, the correct shape of the fixing element is then determined just by viewing the patient's anatomy, and the fixing element can then be produced accordingly. Time-consuming adapting, with the patient open, is no longer required.

Furthermore, the shape of an instruments can be recorded, registered and then navigated, and there exists the possibility of training and/or performing simulations using models.

If a touch screen is used, indications or markings can be made of the touch screen, which can be advantageous for example in craniotomy and for electrodes.

Another field of application relates to adapting the imaging data, captured, for example, in advance from the patient using CT, MR or similar methods. The video camera of the image display device can, for example, record textures of the patient as a video image and therefore improve or "embellish" the data from the imaging. CT or MR tomographs, for example, do not show particularly good patient surface structures. These surface structures, however, are known from the video image and can supplement the tomographic data. In plastic surgery, this can be advantageous when planning surgery and when visually simulating the results of such surgery in advance.

The brightness of the video image can be used to adapt object representation, and, in a further embodiment, the possibility exists of fixing the image display device directly to the image recording apparatus for the internal structures of the patient (CT, MR, fMRI, etc.), in order to simplify associating and/or registering the different image data.

Lastly, it is also possible to simplify operating the input devices in that the portable unit including the image display device and the video camera can be temporarily set or fixed on an arm provided for this purpose and including a mounting, wherein the arm can also be movable.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method for visually combining patient image data from transillumination imaging methods and/or tomographic imaging methods with object image data comprising video images on an image display device coupled to at least one video camera, said method comprising:
    detecting spatial positions of the image display device and/or the video camera and spatial positions of a part of a patient's body via tracking means;
    determining a position of an image plane based on (i) a focal plane of the coupled video camera, (ii) the detected spatial positions of the image display device and/or the coupled video camera, and (iii) the detected spatial position of the part of the patient's body; and
    transmitting an image in the determined image plane from the at least one of (i) transillumination imaging methods and (ii) tomographic imaging methods to the image display device.

2. The method as set forth in claim 1, wherein the image display device and the video camera are formed as a portable unit.

3. The method as set forth in claim 1, further comprising: receiving inputs for image-assisted treatment or treatment planning via an input device on the image display device.

4. The method as set forth in claim 3, wherein an associated computer-assisted treatment planning and assisting system processes the inputs from the input device.

5. The method as set forth in claim 4, wherein treatment-assisting object and/or image information is transmitted via cable-assisted or cable-free data transmission between the image display device and the associated computer-assisted treatment planning and assisting system.

6. The method as set forth in claim 5, wherein the transmitted object and/or image information includes one or more of (i) information on patient-specific parts of the patient's body obtained from two-dimensional or three-dimensional image data; (ii) information on non-patient-specific, model-based object data, (iii) information on implants: (iv) measurement information; (v) information on medicines, medicinal distributions, and simulated distributions; (vi) information on radiosurgical and radiotherapeutic plans; (vii) information on plans for image-assisted surgery (viii) information on registering markers; (ix) information on instruments; and (x) x-ray images artificially generated from digitally reconstructed radiographs and/or information from actual x-ray images.

7. The method as set forth in claim 3, wherein treatment-assisting image or object data or treatment plans are changed or adapted by inputs received via the input device.

8. The method as set forth in any claim 3, further comprising:
    responsive to inputs received via the input device, changing or adapting an image representation displayed on the image display device.

9. The method as set forth in claim 8, further comprising:
    responsive to inputs received via the input device, displaying changes to the patient body predicted by planning.

10. The method as set forth in claim 3, wherein images displayed on the image display device are stored, combined, spliced into image sequences or films, forwarded, played back, subtracted from each other or annotated, responsive to inputs at the input device.

11. The method as set forth in claim 3, further comprising controlling at least one other apparatus in the treatment environment responsive to inputs at the input device.

12. The method as set forth in claim 1, wherein the video image is displayed on a scale of 1:1 with the image in the determined image plane from the at least one of (i) transillumination imaging methods and (ii) tomographic imaging methods.

13. A device for visually combining patient image data from transillumination imaging methods and/or tomographic imaging methods with object image data comprising video images, the device comprising:
    an image display device, the image display device including at least one input device which receives inputs related to image-assisted treatment or treatment planning;
    at least one video camera associated with the image display device as a portable unit, wherein the at least one video camera is attached to the image display device; and
    a computer-assisted navigation system which detects the spatial positions of at least one of (i) the image display device and (ii) the associated video camera and spatial positions of a part of a patient's body.

14. A device for visually combining patient image data from transillumination imaging methods and/or tomographic imaging methods with object image data comprising video images, the device comprising:
    an image display device, the image display device including at least one input device which receives inputs related to image-assisted treatment or treatment planning;

at least one video camera associated with the image display device as a portable unit, wherein the video camera is attached to the image display device; and a computer-assisted navigation system which detects the spatial positions of at least one of the image display device and/or the associated video camera and spatial positions of a part of a patient's body.

15. The device as set forth in claim 14, wherein the input device includes at least one electro-mechanical switch.

16. The device as set forth in claim 14, wherein the input device includes a touch screen.

17. The device as set forth in claim 14, said device being in data communication with a computer-assisted treatment planning and assisting system which processes inputs from the input device.

18. The device as set forth in claim 17, said device further comprising cable-assisted or cable-free data transmission means for transmitting object information between the image display device and the computer-assisted treatment planning and assisting system in response to an input.

19. The method as set forth in claim 17, wherein the image display device is directly attached to an imaging apparatus for the computer-assisted treatment planning and assisting system.

20. The device as set forth in claim 14, wherein the computer-assisted navigation system detects the spatial positions of at least one of (i) the image display device and (ii) the associated video camera and spatial positions of a part of a patient's body via tracking means attached to the image display device and the part of the patient's body.

* * * * *